United States Patent [19]

Brooks et al.

[11] Patent Number: 5,250,565
[45] Date of Patent: * Oct. 5, 1993

[54] INDOLE-, BENZOFURAN-, AND BENZOTHIOPHENE-CONTAINING LIPOXYGENASE-INHIBITING COMPOUNDS

[75] Inventors: Dee W. Brooks; James B. Summers, both of Libertyville, Ill.

[73] Assignee: Abbott Laboratories, Abbott Park, Ill.

[*] Notice: The portion of the term of this patent subsequent to Oct. 10, 2006 has been disclaimed.

[21] Appl. No.: 823,411

[22] Filed: Jan. 21, 1992

Related U.S. Application Data

[63] Continuation of Ser. No. 572,451, Aug. 28, 1990, abandoned, which is a continuation-in-part of Ser. No. 404,300, Sep. 7, 1989, abandoned, which is a continuation-in-part of Ser. No. 138,073, Jan. 11, 1988, Pat. No. 4,873,259, which is a continuation-in-part of Ser. No. 60,784, Jun. 10, 1987, abandoned, which is a continuation-in-part of Ser. No. 12,970, Feb. 10, 1987, abandoned.

[51] Int. Cl.$^5$ .................. A61K 31/38; A61K 31/34; C07D 209/04; C07D 333/52
[52] U.S. Cl. .................. 514/443; 514/415; 514/418; 514/419; 514/469; 514/470; 549/49; 549/51; 549/52; 549/54; 549/55; 549/57; 549/58; 549/462; 549/466; 549/467; 548/484; 548/485; 548/486; 548/469; 548/495
[58] Field of Search .............. 514/415, 418, 419, 443, 514/469, 470; 549/49, 51, 52, 54, 55, 57, 58, 462, 466, 467; 548/484, 485, 486, 469, 495

[56] References Cited

U.S. PATENT DOCUMENTS 4,873,259 10/1989 Summers et al. .................. 514/443

Primary Examiner—Alan Siegel
Attorney, Agent, or Firm—Jerry F. Janssen

[57] ABSTRACT

Pro-drugs of potent 5-lipoxygenase inhibiting compounds comprise compounds of the formula

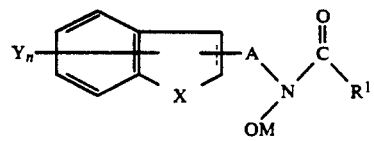

in which A is an alkylene or alkenylene group, X is oxygen, sulfur, sulfoxyl, or substituted nitrogen, and Y is a group which includes substituted or unsubstituted carbocyclic or substituted or unsubstituted heterocyclic aryl. $R^1$ is an alkyl, alkenyl, amino, alkylamino, dialkylamino, or hydroxyamino group or an amine group bearing a metabolically cleavable leaving group. M is hydrogen, a pharmaceutically acceptable cation or a metabolically cleavable leaving group, with the proviso that either M or $R^1$ must bear a metabolically cleavable leaving group.

3 Claims, No Drawings

INDOLE-, BENZOFURAN-, AND BENZOTHIOPHENE-CONTAINING LIPOXYGENASE-INHIBITING COMPOUNDS

CROSS-REFERENCE TO RELATED APPLICATIONS

This is a continuation of application Ser. No. 572,451 filed Aug. 28, 1990, now abandoned which is a continuation-in-part of application Ser. No. U.S. 404,300 filed Sep. 7, 1989, now abandoned which is a continuation-in-part of application of Ser. No. 138,073, filed Jan. 11, 1988, now U.S. Pat. No. 4,873,259, which, in turn, is a continuation-in-part of U.S. application Ser. No. 060,784, filed Jun. 10, 1987, now abandoned, which is a continuation-in-part of U.S. application Ser. No. 012,970, filed Feb. 10, 1987, now abandoned.

TECHNICAL FIELD

This invention relates to organic compounds which inhibit lipoxygenase enzymes, as well as to pro-drug derivatives of such lipoxygenase-inhibiting compounds having metabolically cleavable groups. It also relates to methods and compositions involving inhibiting lipoxygenase enzymes in human and animal hosts in need of such treatment.

BACKGROUND OF THE INVENTION

The lipoxygenases are a family of enzymes which catalyze the oxygenation of arachidonic acid. The enzyme 5-lipoxygenase converts arachidonic acid to 5-hydroperoxyeicosatetraenoic acid (5-HPETE). This is the first step in the metabolic pathway yielding 5-hydroxyeicosatetraenoic acid (5-HETE) and the important class of mediators, the leukotrienes (LTs).

Similarly, 12-and 15-lipoxygenase, convert arachidonic acid to 12-and 15-HPETE, respectively. Biochemical reduction of 12-HPETE leads to 12-HETE, while 15-HPETE is the precursor of the class of biological agents known as the lipoxins.

A variety of biological effects are associated with these products from lipoxygenase metabolism of arachidonic acid and they have been implicated as mediators in various disease states. For example, the leukotrienes $LTC_4$ and $LTD_4$ are potent constrictors of human airways in vitro, and aerosol administration of these substances to non-asthmatic volunteers induces bronchoconstriction. $LTB_4$ and 5-HETE are potent chemotactic factors for inflammatory cells such as polymorphonuclear leukocytes. They also have been found in the synovial fluid of rheumatoid arthritic patients. Leukotrienes have also been implicated as important mediators in asthma, rheumatoid arthritis, gout, psoriasis, allergic rhinitis, adult respiratory distress syndrome, Crohn's disease, endotoxin shock, inflammatory bowel disease and/or ischemia-induced myocardial or brain injury, among others. The biological activity of the leukotrienes has been reviewed by Lewis and Austen (*J. Clinical Invest*, 73: 889 (1984)) and by J. Sirois (*Adv. Lipid Res.* 21: 78 (1985)).

The product 12-HETE has been found in high levels in epidermal tissue of patients with psoriasis. The lipoxins have recently been shown to stimulate elastase and superoxide ion release from neutrophils. Thus, lipoxygenase enzymes are believed to play an important role in the biosynthesis of mediators of asthma, allergy, arthritis, psoriasis, and inflammation. It is postulated that interrupting the biochemical pathways involved in the vanous manifestations of these disease states will provide effective systemic and/or symptomatic treatment of these diseases.

It is therefore an object of this invention to provide compounds which inhibit lipoxygenase enzymes. A further object is the identification of prodrug derivatives of lipoxygenase inhibitors having an added, metabolically cleavable group. By the removal of their cleavable groups, these prodrugs are converted in vivo to active lipoxygenase inhibitors. Such prodrugs have been shown to be useful, for example, in improving the bioavailability of pharmaceuticals by enhancing their solubility, stability, and/or rate of absorption.

SUMMARY OF THE INVENTION

In accordance with the above objects, the present invention provides, in one aspect, 5-and/or 12-lipoxygenase-inhibiting compounds of the formula:

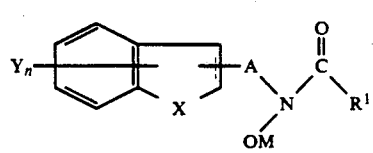

in which the dotted line in the five-member fused ring represents an optional double bond and the group A is selected from the group consisting of alkylene of from one to six carbon atoms, and alkenylene of from two to six carbon atoms.

M is selected from the group consisting of hydrogen, a pharmaceutically acceptable cation, and a metabolically cleavable group.

$R^1$ is selected from the group consisting of hydrogen, alkyl of from one to four carbon atoms, alkenyl of from two to four carbon atoms, and $NR^2R^3$ wherein $R^2$ and $R^3$ are independently selected from hydrogen, alkyl of from one to four carbon atoms, hydroxyl, and a metabolically cleavable group, with the proviso that $R^2$ and $R^3$ are not simultaneously hydroxyl or a metabolically cleavable group.

X is selected from the group consisting of oxygen, sulfur, $SO_2$, and $NR^4$, where $R^4$ is selected from the group consisting of hydrogen, alkyl of from one to six carbon atoms, alkoyl of from one to six carbon atoms, benzoyl, optionally substituted with halogen, hydroxy, alkyl of from one to six carbon atoms, haloalkyl of from one to six carbon atoms, and alkoxy of from one to six carbon atoms, and alkylsulfonyl of from one to six carbon atoms.

The subscript n is an integer of one or two and the group Y is selected independently from the group consisting of (a) hydrogen, (b) halogen, (c) hydroxy, (d) cyano, (e) halosubstituted alkyl of from one to six carbon atoms, (f) alkyl of from one to twelve carbon atoms, (g) alkenyl of from two to twelve carbon atoms, (h) alkoxy of from one to twelve carbon atoms, (i) cycloalkyl of from three to eight carbon atoms, (j) thioalkyl of from one to eight carbon atoms, (k) optionally substituted carbocyclic aryl; (l) optionally substituted (carbocyclic aryl)cycloalkyl in which the cycloalkyl portion may contain from three to eight carbon atoms; (m) optionally substituted (carbocyclic aryl)alkyl in which the alkyl portion may contain from one to six carbon atoms; (n) optionally substituted carbocyclic aryloxyalkyl in which the alkyl portion contains from one to six carbon atoms; (o) optionally substituted (carbocyclic aryl)alkoxyalkyl in which the alkoxyl and alkyl portions may independently contain from one to six carbon atoms; (p) optionally substituted carbocyclic arylthioalkyl in which the alkyl portion may contain from one to six carbon atoms.

In the foregoing, the optional substituents on the carbocyclic aryl groups are selected from the group consisting of (1) alkyl of from one to six carbon atoms, (2) haloalkyl of from one to six carbon atoms, (3) hydroxyalkyl of from one to six carbon atoms, (4) alkoxy of from one to twelve carbon atoms, (5) alkoxyalkoxyl in which the two alkoxy portions may each independently contain from one to six carbon atoms, (6) alkylthio of from one to six carbon atoms, (7) hydroxy, (8) halogen, (9) cyano, (10) carboxyl, and (11) alkoxycarbonyl of from two to eight carbon atoms.

Y is further selected from (q) phenoxy, optionally substituted with a group selected from alkyl of from one to six carbon atoms, haloalkyl of from one to six carbon atoms; alkoxyl of from one to six carbon atoms, hydroxy, and halogen; (r) phenylthio, optionally substituted with a group selected from alkyl of from one to six carbon atoms, haloalkyl of from one to six carbon atoms; alkoxyl of from one to six carbon atoms, hydroxy, and halogen; or a heterocyclic aryl group selected from (s) 2-, 3-, or 4-pyridyl, optionally substituted with a group selected from alkyl of from one to six carbon atoms, haloalkyl of from one to six carbon atoms; alkoxyl of from one to six carbon atoms, hydroxy, and halogen; (t) 2-, 3-, or 4-pyridyloxy, optionally substituted with a group selected from alkyl of from one to six carbon atoms, haloalkyl of from one to six carbon atoms; alkoxyl of from one to six carbon atoms, hydroxy, and halogen; (u) 2-or 3-furyl, optionally substituted with a group selected from alkyl of from one to six carbon atoms, haloalkyl of from one to six carbon atoms, halogen, (v) benzo[b]furyl, optionally substituted with a group selected from alkyl of from one to six carbon atoms, haloalkyl of from one to six carbon atoms; alkoxyl of from one to six carbon atoms, hydroxy, and halogen; (w) 2-or 3-thienyl, optionally substituted with alkyl of from one to six carbon atoms, haloalkyl of from one to six carbon atoms, halogen, phenyl, optionally substituted with alkyl of from one to six carbon atoms, haloalkyl of from one to six carbon atoms, alkoxy of from one to six carbon atoms, hydroxy or halogen; and (x) 2-or 3-benzo [b]thienyl, optionally substituted with alkyl of from one to six carbon atoms, haloalkyl of from one to six carbon atoms; alkoxyl of from one to six carbon atoms, hydroxy, or halogen.

All of the foregoing are with the proviso that at least one of $R^3$ and M is a metabolically cleavable group, said metabolically cleavable group selected from phenylalkoyl in which the alkoyl portion is of from two to six carbon atoms and the phenyl ring is optionally substituted with a group selected from alkyl of from one to six carbon atoms, haloalkyl of from one to six carbon atoms, alkoxy of from one to six carbon atoms, halogen, and hydroxy. Additional metabolically cleavable groups include carboalkoxy of from two to eight carbon atoms, carbamoyl, alkoxyalkyl in which the alkoxy and alkyl groups contain, independently, from one to six carbon atoms, trialkylsilyl in which the alkyl groups are independently selected from alkyl of from one to six carbon atoms, triphenylsilyl, diphenylalkylsilyl in which the alkyl group is selected from alkyl of from one to six carbon atoms, phenyldialkylsilyl in which the alkyl groups are independently selected from alkyl of from one to six carbon atoms, a peptidyl group of from one to five amino acids independently selected from the naturally occurring L-amino acids, and a polysaccharide group comprising 1–5 sugar residues independently selected from the naturally occurring pentoses and hexoses.

DETAILED DESCRIPTION AND PREFERRED EMBODIMENTS

The preferred compounds of the present invention are of formula II:

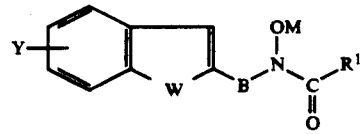

In these preferred compounds W is oxygen or sulfur, B is methylene or $CHCH_3$ and Y and $R^1$ is as defined above. Particularly preferred are hydroxamic acid compounds of formula II where $R^1$ is methyl or ethyl and N-hydroxy urea compounds where $R^1$ is $NR^2R^3$ and $R^2$ and $R^3$ are independently selected from hydrogen and alkyl of from one to four carbon atoms, or where $R^2$ is hydrogen and $R^3$ is a metabolically cleavable group as defined above. M is hydrogen, a pharmaceutically acceptable cation, or a metabolically cleavable group with the proviso that at least one of $R^3$ and M is a metabolically cleavable group.

Examples of compounds which are within the scope of the present invention include, but are not limited to, the following:

N-ethoxycarbonyloxy-N-[1-(benzo[b]thien-2-yl)ethyl]urea;

N-methoxycarbonyloxy-N-[1-(benzo[b]thien-2-yl)ethyl]urea;

N-tert-butoxycarbonyloxy-N-[1-(benzo[b]thien-2-yl)ethyl]urea;

N-thioethylcarbonyloxy-N-[1-(benzo[b]thien-2-yl)ethyl]urea;

N-glutaryloxy-N-[1-(benzo[b]thien-2-yl)ethyl]urea;

N-succinyloxy-N-[1-(benzo[b]thien-2-yl)ethyl]urea;

N'-acetyl-N-hydroxy-N-[1-(benzo[b]thien-2-yl)ethyl]urea; and

N'-carbamoyl-N-hydroxy-N-[1-(benzo[b]thien-2-yl)ethyl]urea.

The N'-carbamoyl pro-drug derivative is particularly preferred.

Certain compounds of the present invention contain one or more asymmetric carbon atoms, giving rise to enantiomeric and diastereomeric forms of the compounds. In addition, certain compounds of this invention contain a carbon-carbon double bond, giving rise to cis-and trans-geometric isomers. It is to be understood that the invention encompasses the enantiomers, diastereomers, and geometric isomers as well as mixtures thereof including racemic mixtures.

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

"Alkylamino" and "dialkylamino" refer, respectively, to one or two alkyl groups, as defined above, attached to the parent molecular moiety through a nitrogen atom and are represented by methyl amino, dimethylamino, ethyl- and diethylamino, methylethylamino, and the like.

The term "cycloalkyl" denotes a monovalent group derived from a monocyclic or bicyclic saturated carbocyclic ring compound by the removal of a single hydrogen atom. Examples include cyclopropyl, cyclobutyl, cycopentyl, cyclohexyl, bicyclo[2.2.1]heptanyl, and bicyclo[2.2.2]octanyl.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkyl" refers to an alkoxy group, as defined above, attached through an alkylene group to the parent molecular moiety.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocaron containing at least one carbon-carbon double bond. Examples of alkenylene include —CH=CH—, —CH₂CH=CH—, —C(CH₃)=CH—, —CH₂CH=CHCH₂—, and the like.

The terms "alkanoyl" and "alkoyl" represent an alkyl group, as defined above, attached to the parent molecular moiety through a carbonyl group. Alkanoyl (or alkoyl) groups are exemplified by formyl, acetyl, propionyl, butanoyl and the like.

"Alkanoylamino" refers to an alkanoyl group, as defined above, attached to the parent molecular moiety through an amino group and is represented by such groups as acetylamino, propionylamino, and the like.

The term "N-alkanoyl-N-alkylamino" denotes a nitrogen atom attached to the parent molecular moiety which nitrogen atom bears an alkanoyl group and an alkyl group, as those terms are defined above. N-alkanoyl-N-alkylamino groups are exemplified by N-acetyl-N-methylamino, N-propionyl-N-ethylamino, and the like.

"Alkylaminocarbonyl" and "dialkylaminocarbonyl" represent, respectively, an alkylamino or dialkylamino group attached to the parent molecular moiety through a carbonyl group. Such groups include, for example methylaminocarbonyl, ethylaminocarbonyl, dimethylaminocarbonyl, diethylaminocarbonyl, methylethylaminocarbonyl, and the like.

The term "alkoxycarbonyl" represents an ester group; i.e. an alkoxy group, attached to the parent molecular moiety through a carbonyl group such as methoxycarbonyl, ethoxycarbonyl, and the like.

The term "carbamoyl" denotes a group of the formula —C(O)NRR' where R and R' are independently selected from hydrogen or alkyl of from one to six carbon atoms.

The term "carbocyclic aryl" denotes a monovalent carbocyclic ring group derived by the removal of a single hydrogen atom from a monocyclic or bicyclic fused or non-fused ring system obeying the "$4n+2\pi$ electron" or Huckel aromaticity rule. Examples of carbocyclic aryl groups include phenyl, 1- and 2-naphthyl, biphenylyl and the like.

The term "(carbocyclic aryl)alkyl" refers to a carbocyclic ring group as defined above, attached to the parent molecular moiety through an alkylene group. Representative (carbocyclic aryl)alkyl groups include phenylmethyl or benzyl, phenylethyl, phenylpropyl, 1-naphthylmethyl, and the like.

The term "carbocyclic aryloxyalkyl" refers to a carbocyclic aryl group, as defined above, attached to the parent molecular moiety through an oxygen atom and thence through an alkylene group. Such groups are exemplified by phenoxymethyl, 1- and 2-naphthyloxymethyl, phenoxyethyl and the like.

The term "(carbocyclic aryl)alkoxyalkyl" denotes a carbocyclic aryl group as defined above, attached to the parent molecular moiety through an alkoxyalkyl group. Representative (carbocyclic aryl)alkoxyalkyl groups include phenylmethoxymethyl, phenylethoxymethyl, 1- and 2-naphthylmethoxyethyl, and the like.

"Carbocyclic arylthioalkyl" represents a carbocyclic aryl group as defined above, attached to the parent molecular moeity through a sulfur atom and thence through an alklyene group and are typified by phenylthiomethyl, 1- and 2-naphthylthioethyl and the like.

The term "carbocyclic arylaminoalkyl" refers to a carbocyclic aryl group as defined above, attached to the parent molecular moiety through a -NH-alkylene-group and is exemplified by phenylaminomethyl, phenylaminoethyl, 1- and 2-naphthylaminomethyl and the like.

"[N-(carbocyclic aryl)-N-alkylamino]alkyl" refers to a group attached to the parent molecular moiety through an aminoalkyl group in which a carbocyclic aryl group, as defined above, and an alkyl group, as defined above, are attached to the nitrogen atom and includes such representative examples as (N-phenyl-N-methylamino)methyl, (N-phenyl-N-ethylamino)methyl, (N-(1-naphthyl)-N-propylamino)ethyl and the like.

"[N-(carbocyclic arylalkyl)amino]alkyl" denotes a carbocyclic arylalkyl group, as defined above, attached to the parent molecular moiety through an aminoalkyl group and is typified by [N-(phenylmethyl)amino]methyl, [N-(phenylethyl)amino]methyl, (1- and (2-naphthylmethylamino)methyl and the like.

"[N-(carbocyclic arylalkyl)-N-alkylamino]alkyl" refers to a group attached to the parent molecular moiety through an aminoalkyl group and having attached to the nitrogen atom thereof a carbocyclic arylalkyl group, as defined above, and an alkyl group. [N-(carbocyclic arylalkyl)-N-alkylamino]alkyl groups are represented by [N-phenylmethyl-N-methylamino]methyl, [N-phenylethyl-N-methylamino]propyl, [N-(1-naphthylmethyl)-N-ethylamino]methyl, and the like.

The term "pharmaceutically acceptable cation" refers to non-toxic cations, including but not limited to cations based on the alkali and alkaline earth metals, such as sodium, lithium, potassium, calcium, magnesium, and the like, as well as non-toxic ammonium, quaternary ammonium, and amine cations, including but not limited to ammonium, tetramethylammonium, tetraethylammonium, methylamine, dimethylamine, trimethylamine, triethylamine, ethylamine, and the like.

The term "metabolically cleavable group" as used herein denotes a moiety which is readily cleaved in vivo from the compound to which it is attached, which compound (after cleavage) remains or becomes physiologically active. Metabolically cleavable groups included, but are not limited to, such groups as alkoyl, benzoyl, 1- and 2-naphthoyl, phenylalkoyl, carboalkoxy, carbamoyl, alkoxymethyl, trialkylsilyl, triphenylsilyl, diphenyl(alkyl)silyl, peptidyl groups of 1-5 amino acid residues selected from the naturally occurring alpha-amino acids, and polysacharide moieties comprising 1-5 sugar residues selected from the naturally occurring sugars. Examples of specific metaboliccaly cleavable groups include, but are not limited to, acetyl, propionyl, oxalyl, malonyl, fumaryl, succinyl, glutaryl, benzoyl, o-, m- and p-aminobenzoyl, o-, m- and p-carboxybenzoyl, 3-pyridinecarboxylic acid, 2-indolyl, phenylacetyl, methoxycarbonyl, tert-butoxycarbonyl, iso-butoxycarbonyl, carbamoyl, dimethylcarbamoyl, methoxymethyl, ethoxymethyl, trimethylsilyl, dimethyl-tert-butylsilyl, triphenylsilyl, diphenyl-tert-butylsilyl, glycyl, alanyl, histidyl, glutamyl, lysyl, alanylalanyl, glycylisoleucyl, aspartylalanylglycyl, glucosyl, galactosyl, sucrosyl, and the like.

The term "peptidyl" group as used through this specification and the appended claims means a single amino acid, connected to the parent molecular moeity through its C-terminus or, two or more amino acids linked by peptide bonds and attached to the parent molecular moiety through its C-terminus. The amino acids are selected from the naturally occurring L-amino acids.

Because of the ease with which the metabolically cleavable groups of the inventive compounds are removed in vivo, these compounds may act as prodrugs of other lipoxygenase inhibitors. The inventive compounds therefore have the advantage that, in addition to themselves being active inhibitors of lipoxygenase enzymes, they are converted in vivo to active lipoxygenase-inhibiting residues. Moreover, as prodrugs the compounds of the present invention may exhibit improved bioavailability as a result of enhanced solubility and/or rate of absorbtion.

METHOD OF TREATMENT

The compounds of the invention inhibit lipoxygenase activity, which makes the compounds useful in the treatment and prevention of disease states in which lipoxygenase may be involved, including, but not limited to, asthma, rheumatoid arthritis, gout, psoriasis, allergic rhinitis, allergic dermatitis, inflammatory disorders of the skin, acne, adult respiratory distress syndrome, Crohn's disease, endotoxin shock, inflammatory bowel disease and/or ischemia-induced myocardial or brain injury. The compounds of the invention inhibit oxidative modification of lipids which makes them useful in diseases such as atherosclerosis. In some cases this will involve preventing the underlying cause of the disease state and in other cases, while the underlying disease will not be affected, the compounds of this invention will have the benefit of ameliorating the symptoms or preventing the manifestations of the disease.

Accordingly, this invention provides a method of treatment for inhibiting 5- and/or 12-lipoxygenase activity in a human or lower animal host in need of such treatment, which method comprises administration to the human or lower animal host of a compound of the invention in a therapeutically effective amount to inhibit lipoxygenase activity in the host. This invention also provides a method of treating asthma, rheumatoid arthritis, gout, psoriasis, allergic rhinitis, allergic dermatitis, inflammatory disorders of the skin, acne, atherosclerosis, adult respiratory distress syndrome, Crohn's disease, endotoxin shock, inflammatory bowel disease and/or ischemia-induced myocardial or brain injury in a human or lower animal in need of such treatment comprising administering to the human or lower animal a therapeutically effective amount of a compound described above. Further, this invention also provides a method of treating or preventing the symptoms of the disease states mentioned above.

The compounds of the present invention may be administered orally, parenterally or topically in dosage unit formulations containing conventional nontoxic pharmaceutically acceptable carriers, adjuvants and vehicles as desired.

The term "parenterally" as used herein includes subcutaneous, intravenous, intra-arterial injection or infusion techniques, without limitation. The term "topically" encompasses administration rectally and by inhalation spray, as well as by the more common routes of the skin and the mucous membranes of the mouth and nose.

Total daily dose of the compounds of this invention administered to a host in single or divided doses may be in amounts, for example, of from about 0.001 to about 100 mg/kg body weight daily and more usually 0.1 to 35 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

FORMULATION OF PHARMACEUTICAL COMPOSITION

This invention also provides pharmaceutical compositions in unit dosage form for the inhibition of 5- or 12-lipoxygenase activity in a human or lower animal host in need of such treatment, comprising a compound of this invention and one or more nontoxic pharmaceutically acceptable carriers, adjuvants or vehicles. The amount of active ingredient that may be combined with such materials to produce a single dosage form will vary depending upon various factors, as indicated above.

A variety of materials can be used as carriers, adjuvants and vehicles in the composition of this invention, as available in the pharmaceutical arts. Injectable preparations, such as oleaginous solutions, suspensions or emulsions, may be formulated according to known art, using suitable dispersing or wetting agents and suspending agents, as needed. The sterile injectable preparation may employ a nontoxic parenterally acceptable diluent or solvent as, for example, sterile nonpyrogenic water or 1,3-butanediol.

Among the other acceptable vehicles and solvents that may be employed are 5% dextrose injection, Ringer's injection and isotonic sodium chloride injection (as described in the USP/NF). In addition, sterile, fixed oils are conventionally employed as solvents or suspending media. For this purpose any bland fixed oil may be used, including synthetic mono-, di- or triglycerides. Fatty acids such as oleic acid can also be used in the preparation of injectable compositions.

Suppositories for rectal administration of the compound of this invention can be prepared by mixing the drug with suitable nonirritating excipient such as cocoa butter and polyethylene glycols, which are solid at ordinary temperatures but liquid at body temperature and which therefore melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsules, tablets and pills, the dosage forms may also comprise buffering agents. Solid oral preparations can also be prepared with enteric or other coatings which modulate release of the active ingredients. Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying suspending, sweetening, flavoring and perfuming agents.

SYNTHESIS OF THE COMPOUNDS

Several synthetic methods may be used to prepare compounds of this invention. Some of these methods are described by schemes 1-6 below. Although in each case the sequence is illustrated with a compound of formula I wherein $R^1$ is methyl or $NH_2$, A is —CHCH3—, X is sulfur, and Y is hydrogen, it will be seen from the examples that other compounds of this invention can be prepared in the same manner using the appropriate starting materials. Compounds of formula I wherein $R^1$ is alkyl, alkenyl, N(alkyl)$_2$ or hydrogen may be prepared as described in Scheme 1.

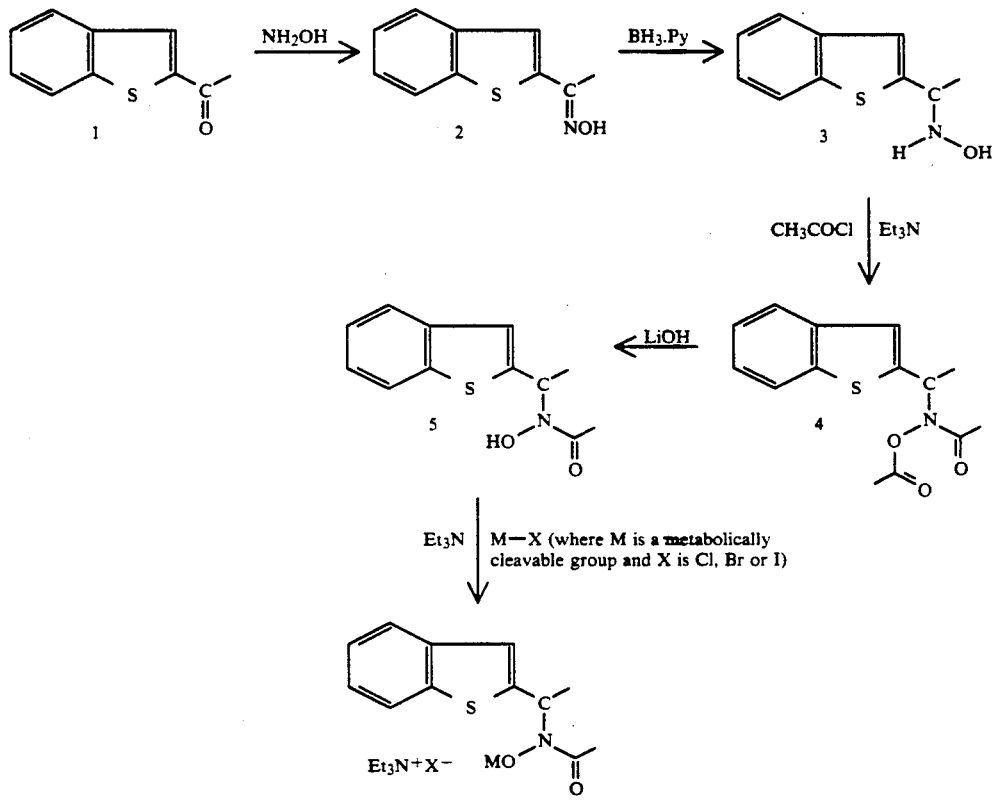

In scheme 1,2-acetyl benzo[b]thiophene, 1, is treated with hydroxylamine in ethano/pyridine to produce e the oxime 2. This is reduced to the hydroxylamine 3 with borane pyridine complex and then converted to the N,O-diacetate 4 with acetyl chloride and triethylamine. The diacetate is converted to the hydroxamic acid 5 by hydrolysis with lithium hydroxide. The hydroxamic acid, 5, can be treated with various electrophilic reagents, M-X, to provide derivatives where M is a metabolically cleavable group as previously defined.

Compounds of formula I wherein $R^1$ is $NR^2R^3$ can be prepared according to the method outlined in scheme 2, below.

Scheme 2

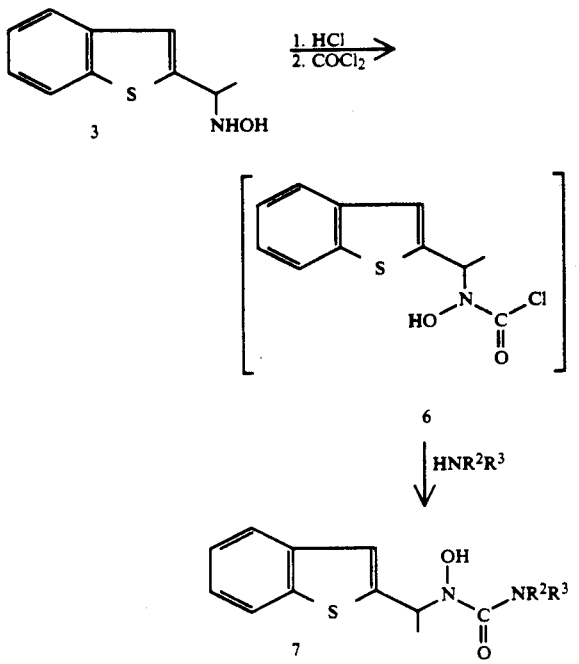

Hydroxylamine 3, the synthesis of which was described above, is treated with gaseous HCl followed by phosgene. The resulting putative carbamoyl chloride 6 is reacted without isolation with aqueous ammonia to yield the urea 7.

Compounds of formula I, wherein $R^1$ is $NR^2R^3$ and wherein $R^2$ is hydrogen and $R^3$ is a metabolically cleavable group can also be prepared according to Scheme 3, below.

Scheme 3

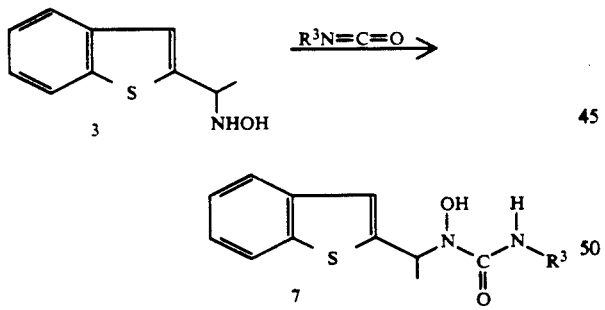

Hydroxylamine 3 is treated with an isocyanate ($R^3$NCO), followed by ammonium chloride workup to give the urea 7.

EXAMPLE 1

N-hydroxy-N-(1-benzo[b]thien-2-ylethyl)acetamide a. 2-Acetyl benzo[b]thiophene.

Method a. Using the method described in Scheme 1, benzo[b]thiophene (10 g, 75 mmole) was dissolved in THF (50 mL) and cooled to $-78°$ C. Butyl lithium (28 mL, 2.7M in hexanes) was added. The mixture was stirred for 15 minutes and N,O-dimethyl acetohydroxamic acid was added. Following an additional 30 minutes of stirring, the reaction was quenched at $-78°$ C. with ethanol and 2N HCl solution and extracted into ether. The solvent was removed in vacuo and the residue chromatographed on silica gel eluting with 20% ether in pentane to yield 6.9 g of the desired product as a white solid.

Method b. To a solution of benzo[b]thiophene (10.0 g, 75 mmole) in THF (50 mL) was added n-butyl lithium (33 mL, 2.5M in hexanes) at $-70°$ C. under $N_2$. The mixture, containing a white precipitate, was stirred at $-70°$ C. for 1 hour. Acetaldehyde (4.6 mL, 82 mmole) was added dropwise. After a few minutes the reaction was quenched with saturated $NH_4Cl$ solution. The layers were separated, the organic layer dried over $MgSO_4$, filtered, and evaporated to give a white solid (10 g) which was used directly for the next step.

The alcohol prepared as described above (1.0 g) in acetone (50 mL) was cooled to 5° C. and Jones Reagent was added dropwise until the orange yellow color persisted (1.4 mL). The reaction mixture was diluted with water and the desired product precipitated. It was collected by filtration to give 0.85 g.

b. 2-Acetyl benzo[b]thiophene oxime.

2-Acetyl benzo[b]thiophene (5 g, 28.4 mmole), prepared as described in step a above, and hydroxylamine hydrochloride 3.0 g, 42.6 mmole) were dissolved in a mixture of ethanol (50 mL) and allowed to stir at room temperature for 2 hours. Most of the solvent was removed in vacuo and the residue dissolved in ether. After washing with 2N HCl (100 mL), the solution was dried over $MgSO_4$ and evaporated. A white crystalline solid was obtained and was carried on without further purification.

An alternative work-up was also used. The reaction mixture was diluted with water (300 mL) and the product precipitated. It was filtered off and dried in vacuo.

c. 1-Benzo[b]thien-2-ylethyl hydroxylamine.

The oxime prepared as in step b above (3.5 g, 18.5 mmole) was dissolved in ethanol (25 mL) and cooled to 0° C. Borane pyridine complex (3.7 mL, 37 mmole) was added via syringe under nitrogen followed ten minutes later by 20% HCl in ethanol (30 mL). Within thirty minutes the reaction was complete and was brought to pH 9 with the addition of solid sodium carbonate or 2N NaOH. The mixture was extracted into ether and dried over $MgSO_4$. After evaporation a white solid (3.0 g) was obtained. This was carried on without further purification.

d. N-Acetoxy-N(1-benzo[b]thien-2-ylethyl) acetamide.

The hydroxylamine (1.0 g, 5.2 mmole) prepared as in step c above and pyridine (1.0 mL, 13 mmole) were dissolved in tetrahydrofuran (40 mL) and cooled to 0° C. Acetyl chloride (1.0 mL, 13 mmole) was added slowly. After stirring for 30 minutes the reaction mixture was washed with 2N HCl, dried over MgSO4 and evaporated.

e. N-hydroxy-N-(1-benzo[b]thien-2-ylethyl)acetamide.

The material obtained in the previous step (1.0 g) was dissolved in isopropyl alcohol (10 mL) and lithium hydroxide (1.0 g) in water (10 mL). After stirring for thirty minutes, most of the solvent was removed in vacuo. The residue was neutralized with 2N HCl, extracted with ether, and the organic phase was then dried over MgSO4 and evaporated. The desired product was obtained as a white crystalline solid (750 mg) following silica gel chromatography. ($R^1$=CH_3, A=CHCH_3, X=S, Y=H).

Melting Point: 108°-110° C.

NMR (300 MHz, DMSO-d6): 1.56 (d, 3H); 2.02 (s, 3H); 5.90 (m, 1H); 7.29-7.38 (m, 3H); 7.75-7.92 (m, 2H); 9.75 (brs, 1H).

Mass spectrum (EI): 235 M+, 218,176,161,128.

EXAMPLE 2

N-hydroxy-N-(1-benzo[b]thien-2-ylethyl)urea

Method a. Using the method of Scheme 3, 1-benzo[b]thien-2-ylethyl hydroxylamine prepared as described in Example 1, step c (2.0 g, 10 mmole), was refluxed for thirty minutes with trimethylsilyl isocyanate (1.65, 14.2 mmole) in dioxane (30 mL). The reaction mixture was then washed with saturated NH4Cl solution, dried with MgSO4, and evaporated.

Method b. Using the method of Scheme 2, 1-benzo[b]thien-2-ylethyl hydroxylamine prepared as described in example 1, step c, was dissolved in toluene (100 mL) and HCl gas was bubbled through the mixture at a moderate rate for about four minutes. The solution was then heated to reflux and phosgene was bubbled through for another four minutes. After an additional one hour reflux, the mixture was allowed to cool to room temperature and then added to excess cold ammonium hydroxide solution. The precipitate was collected and recrystallized. ($R^1$=NH2, A=CHCH3, X=S [2-isomer], Y=H).

Melting Point: 157°-158° C.

NMR (300 MHz, DMSO-d6): 1.51 (d, 3H); 5.55 (q, 1H); 6.45 (brs, 2H); 7.25-7.37 (m, 3H); 7.75-7.91 (m, 2H); 9.35 (s, 1H).

Mass spectrum (CI-NH3): 237 (M+1)+, 221,194,176,161.

EXAMPLE 3

N-acetoxy-N-[1-(benzo[b]thien-2-yl)ethyl]urea

To a stirred solution of N-hydroxy-N-1-(benzo[b]thien-2ylethyl) urea (product of Example 2, 0.80 g, 3.4 mmol) in THF (20 mL) at 0° C. was added triethylamine (0.52 mL, 3.7 mmol) followed by acetyl chloride (0.27 mL, 3.7 mmol). The reaction stirred until complete before quenching with water. The layers were separated and the aqueous layer was extracted with ethyl acetate (3×50 mL). The organics were combined, dried, and evaporated. The solid obtained was recrystallized to constant melting point using ethyl acetate:-hexane. The title compound was prepared in a 68% yield. ($R^1$=NH2 A=CHCH3, X=S [2-isomer], Y=H, M=COCH3).

M.P.=138° C.; 1H

NMR (300 MHz, DMSO-d6); 1.50 (3H, d), 2.12 (3H, br.s), 5.69 (1H, m), 6.86 (2H, br.s), 7.34 (3H, m), 7.80 (1H, m), 7.91 (1H, m); MS (M+NH4)+ =296, (M+H)+ =279.

EXAMPLE 4

N-ethoxycarbonyloxvyN-[1-(benzo[b]thien-2-yl)ethyl]urea

To a solution of N-hydroxy-N-(benzo[b]thien-2ylethyl) urea (product of Example 2, 2.00 g, 8.5 mmol) and triethylamine (944 mg, 9.35 mmol) in CH2Cl2 (40 mL), was added dropwise ethylchloroformate (1.01 g, 9.35 mmol). Upon completion of addition, the reaction was stirred for 10 min. It was then diluted with brine (40 mL) and the layers were separated. The aqueous was extracted with CH2Cl2 (2×40 mL). The organics were combined, dried with MgSO4 and concentrated. The resulting residue was crystallized in ethylacetate/hexanes to afford the desired product as a white solid. ($R^1$=NH2, A=CHCH3, X=S [2-isomer], Y=H, M=OCO2CH2CH3).

M.P.=140°-141° C.; 1H

NMR (300 MHz, DMSO-d6): 0.92-1.34 (bm, 3H), 1.54 (d, 3H, J=7.5 Hz), 3.92-4.34 (m, 2H), 5.70 (m, 1H), 6.98 (bs, 2H), 7.29-7.39 (m, 3H), 7.81 (m, 1H), 7.91 (m, 1H);

Mass spectrum (M+H)+ =309.

Analysis calc'd for $C_{14}H_{16}N_2O_4S$: C=54.53, H=5.23, N=9.09; Found: C=54.20, H=5.16, N=9.07.

EXAMPLE 5

N-methoxycarbonyloxy-N-[1-(benzo[b]thien-2-yl)ethyl]urea

The desired material was prepared according to the procedure of Example 4 substituting methyl chloroformate for ethyl chloroformate. ($R^1$=NH2 A=CHCH3, X=S [2-isomer], Y=H, M=OCO2CH3).

M.P.=124°-125° C.

NMR (300 MHz, DMSO-d6): 1.53 (d, 3H, J=7 Hz), 3.78 (m, 3H), 5.70 (m, 1H), 6.99 (bs, 2H), 7.35 (m, 3H), 7.81 (m, 1H), 7.91 (m, 1H).

Mass spectrum (M+H)+ =295.

Analysis calc'd for $C_{13}H_{14}N_2O_4S$: C=53.05, H=4.79, N=9.52; Found: C=53.13, H=4.79, N=9.51.

EXAMPLE 6

N-tert-butoxycarbonyloxy-N-[1-(benzo[b]thien-2-yl)ethyl]urea

The desired material was prepared according to the procedure of Example 4 substituting di-tert-butyldicarbonate for ethyl chloroformate. ($R^1$=NH2, A=CHCH3, X=S [2-isomer], Y=H, M=OCO2(CH3)3.

M.P.=120°-122° C.

NMR (300 MHz, DMSO-d6): 1.10-1.49 (m, 9H), 1.52 (d, 3H, J=7 Hz), 5.69 (m, 1H), 6.89 (bs, 2H), 7.34 (m, 3H), 7.81 (m, 1H), 7.91 (m, 1H).

Mass spectrum: (M+H)+ =337.

Analysis calc'd for $C_{16}H_{20}N_2O_4S$: C=57.12, H=5.99, N=8.33; Found: C=57.14, H=6.04, N=8.30.

EXAMPLE 7

N-thioethylcarbonyloxy-N-[1-(benzo[b]thien-2-yl)ethyl]urea

The desired material was prepared according to the procedure of Example 4 substituting ethyl chlorothiolformate for ethyl chloroformate. ($R^1$=NH2 A=CHCH3, X=S [2-isomer], Y=H, M=OCO2CH2CH3).

M.P.=130°-132° C.

NMR (300 MHz, DMSO-d6): 0.70-1.33 (m, 3H), 1.58 (d, 3H, J=7 Hz), 2.59-2.97 (m, 2H), 5.69 (m, 1H), 7.10 (bs, 2H), 7.29-7.40 (m, 3H), 7.81 (m, 1H), 7.93 (m, 1H).

Mass spectrum: (M+H)+ =325.

Analysis calc'd for $C_{14}H_{16}N_2O_3S_2$: C=51.83, H=4.97, N=8.64; Found: C=52.01, H=4.97, N=8.68.

EXAMPLE 8

N-glutaryloxy-N-[1-(benzo[b]thien-2-yl)ethyl]urea

The desired material was prepared according to the procedure of Example 3 substituting glutaric anhydride for acetyl chloride. ($R^1$=NH2, A=CHCH3, X=S [2-isomer], Y=H, M=OCO(CH2)3CO2H).

M.P.=129.5°-130.5° C.

NMR (300 MHz, DMSO-d6): 1.49 (d, 3H, J=7 Hz), 1.74 (m, 2H), 2.23 (m, 2H), 2.51 (under DMSO-2H), 5.69 (m, 2H), 6.86 (bs, 2H), 7.35 (m, 3H), 7.80 (m, 1H), 7.91 (m, 1H), 12.13 (bs, 1H).

Mass spectrum: (M+H)+ = 351.

Analysis calc'd for $C_{16}H_{18}N_2O_5S$: C=54.84, H=5.18, N=8.00; Found: C=54.71, H=5.29, N=7.91.

EXAMPLE 9

N-succinyloxy-N-[1-(benzo[b]thien-2-yl)ethyl]urea

The desired material was prepared according to the procedure of Example 3 substituting succinic anhydride for acetyl chloride. ($R^1$=NH_2, A=CHCH_3, X=S[2-isomer], Y=H, M=OCO(CH_2)_3CO_2H).

M.P. 127.5°-129.0° C.

NMR (300 MHz, DMSO-d6): 1.51 (d, 3H, J=7 Hz), 2.54 (m, 2H), 2.69 (m, 2H), 5.71 (m, 1H), 6.81 (bs, 2H), 7.35 (m, 3H), 7.80 (m, 1H), 7.91 (m, 1H), 12.45 (bs, 1H).

Mass spectrum: (M+H)+ = 337.

Analysis calc'd for $C_{15}H_{16}N_2O_5S$: C=53.56, H=4.80, N=8.33; Found: C=53.37, H=4.96, N=8.33.

EXAMPLE 10

N'-acetyl-N-hydroxy-N-[1-(benzo[b]thien-2-yl)ethyl]urea

To a solution of N-(1-benzo[b]thien-2-yl)ethylhydroxylamine (1.50 g, 7.8 mmol) in THF (25 mls) was added acyl isocyanate (37 mL of a 0.25M solution in ether, 9.3 mmol). The reaction was stirred for 15 min, then diluted with brine (25 mL). This aqueous solution was extracted with ethylacetate (3×25 mL). The organics were combined, dried with MgSO_4 and concentrated. Crystallization in ether:hexanes afforded the desired product. ($R^1$=NHCOCH_3, A=CHCH_3, X=S [2-isomer], Y=H, M=H).

M.P.=134.0°-136.5° C.

NMR (300 MHz, DMSO-d6): 1.59 (d, 3H, J=7 Hz), 2.25 (s, 3H), 5.69 (q, 1H J=7 Hz), 7.34 (m, 3H), 7.80 (m, 1H), 9.38(bs, 1H), 9.98 (bs, 1H).

Mass spectrum: (M+H)+ = 279,

Analysis calc'd for $C_{13}H_{14}N_2O_3S$: C=56.10, H=5.07, N=10.07; Found: C=56.14, H=5.18, N=10.10.

EXAMPLE 11

N'-carbamoyl-N-hydroxy-N-[1-(benzo[b]thien-2-yl)ethyl]urea

To a stirred solution of urea (7.27 g, 119 mmol) was added phenyl chloroformate (8.9 g, 57 mmol) followed by pyridine (30 mL). The resulting mixture became highly exothermic and soon solidified. This solid residue was dispersed and washed well with pyridine and ethylacetate to afford the intermediate N-phenoxycarbamoyl urea. A solution of N-(1-benzo[b]thien-2-yl)ethylhydroxylamine (0.50 g, 2.6 mmol) and N-phenoxycarbamoyl urea (0.46 g, 2.6 mmol) in dioxane (12 mL) was heated at 50° C. for 18 h. The mixture was then brought to 75° C. for 24 h. The reaction was cooled to r.t. and concentrated in vacuo. The resulting residue was crystallized in ethanol:hexanes to afford the desired product. ($R^1$=NHCONH_2, A=CHCH_3, X=S [2-isomer], Y=H, M=H).

M.P.=180° C. (dec).

NMR (300 MHz, DMSO-d6): 1.59 (d, 3H, J=7 Hz), 5.67 (q, 61 1Hm, J=7 Hz), 7.15 (bs, 1H), 7.33 (m, 3H), 7.65 (bs, 1H), 7.80 (m, 1H), 7.91 (m, 1H), 8.49 (bs, 1H), 10.01 (bs, 1H).

Mass spectrum: (M+H)+ = 280.

Lipoxygenase IC_{50} Determination

Assays to determine 5-lipoxygenase inhibitory activity were performed in 200 microL incubations containing the 20,000×g supernatant from 6×10^4 homogenized RBL-1 cells, 2% DMSO vehicle and various concentrations of the test compound. Reactions were initiated by addition of radiolabelled arachidonic acid and terminated by acidification and ether extraction. Reaction products were separated from nonconverted substrate by thin layer chromatography and measured by liquid scintillation spectroscopy. All treatments were evaluated in triplicate incubations. Inhibition of 5-lipoxygenase activity was computed by comparison of the quantity of products formed in the treatment incubations to the mean product formation in vehicle control groups (n=8). IC_{50} values and 95% confidence limits were computed by linear regression analysis of percentage inhibition versus log inhibitor concentration plots. Inhibitory potencies for representative examples of compounds of this invention are listed in Table 1.

TABLE 1

| In vitro 5-lipoxygenase Inhibitory Potency of Compounds of this Invention. | | | | | | | |
|---|---|---|---|---|---|---|---|
| Ex. | $R^1$ | A | Z | M | X | Y | Attached* IC_{50} (μM) |
| 1 | CH_3 | CHCH_3 | 0 | H | S | H | 2  1.1 |
| 2 | NH_2 | CHCH_3 | 0 | H | S | H | 2  0.65 |
| 3 | NH_2 | CHCH_3 | 0 | C(O)CH3 | S | H | 2  2.1 |
| 4 | NH_2 | CHCH_3 | 0 | C(O)OCH2CH3 | S | H | 2  1.5 |
| 5 | NH_2 | CHCH_3 | 0 | COOCH3 | S | H | 2  1.2 |
| 9 | NH_2 | CHCH_3 | 0 | C(O)CH2CH2COOH | S | H | 2  0.6 |
| 10 | NHC(O)CH3 | CHCH_3 | 0 | H | S | H | 2  1.5 |
| 11 | NHC(O)NH2 | CHCH_3 | O | H | S | H | 2  1.0 |

*Position at which side chain is attached to the heterocyclic ring system.

The foregoing examples are merely illustrative of the invention and are not intended to limit the invention to the disclosed compounds. Variations and changes which are obvious to one skilled in the art are intended to be within the scope and nature of the invention which are defined in the appended claims.

We claim:

1. A compound selected from the group consisting of
N-ethoxycarbonyloxy-N-[1-(benzo[b]thien-2-yl)ethyl]urea;
N-methoxycarbonyloxy-N-[1-(benzo[b]thien-2-yl)ethyl]urea;
N-tert-butoxycarbonyloxy-N-[1-(benzo[b]thien-2-yl)ethyl]urea;
N-thioethylcarbonyloxy-N-[1-(benzo[b]thien-2-yl)ethyl]urea;
N-glutaryloxy-N-[1-(benzo[b]thien-2-yl)ethyl]urea;
N-succinyloxy-N-[1-(benzo[b]thien-2-yl)ethyl]urea;

N'-acetyl-N-hydroxy-N-[1-(benzo[b]thien-2-yl)ethyl]urea; and

N'-carbamoyl-N-hydroxy-N-[1-(benzo[b]thien-2-yl)ethyl]urea.

2. A pharmaceutical composition for inhibiting lipoxygenase enzymes comprising a therapeutically effective amount of a compound as defined by claim 1 in combination with a pharmaceutically acceptable carrier.

3. A method of inhibiting lipoxygenase enzymes in a host mammal in need of such treatment comprising administering to such a mammal a therapeutically effective amount of a compound as defined by claim 1.

* * * * *